US00PP17977P2

(12) United States Plant Patent
Horvath

(10) Patent No.: US PP17,977 P2
(45) Date of Patent: Sep. 4, 2007

(54) ***SALVIA* PLANT NAMED 'GOLDEN DELICIOUS'**

(50) Latin Name: *Salvia elegans*
Varietal Denomination: Golden Delicious

(76) Inventor: Brent A. Horvath, 285 Church Dr., Fontana, WI (US) 53125

( * ) Notice: Subject to any disclaimer, the term of this patent is extended or adjusted under 35 U.S.C. 154(b) by 0 days.

(21) Appl. No.: 11/349,670

(22) Filed: Feb. 7, 2006

(51) Int. Cl.
*A01H 5/00* (2006.01)

(52) U.S. Cl. ..... Plt./226
(58) Field of Classification Search ..... Plt./226
See application file for complete search history.

*Primary Examiner*—Kent Bell
(74) *Attorney, Agent, or Firm*—C. A. Whealy

(57) ABSTRACT

A new and distinct cultivar of *Salvia* plant named 'Golden Delicious', characterized by its upright plant habit; freely branching habit; yellow green-colored foliage; and numerous large red-colored flowers.

1 Drawing Sheet

Botanical designation: *Salvia elegans.*
Cultivar denomination: 'Golden Delicious'.

BACKGROUND OF THE INVENTION

The present Invention relates to a new and distinct cultivar of *Salvia* plant, botanically known as *Salvia elegans,* and hereinafter referred to by the name 'Golden Delicious'.

The new *Salvia* is a naturally-occurring whole plant mutation of an unnamed selection of *Salvia elegans,* not patented. The new *Salvia* was discovered and selected by the Inventor during the fall of 2001 from within a population of plants of the parent selection in a controlled environment in Hebron, Ill.

Asexual reproduction of the new cultivar by cuttings at Hebron, Ill., since February, 2002, has shown that the unique features of this new *Salvia* are stable and reproduced true to type in successive generations.

SUMMARY OF THE INVENTION

Plants of the cultivar Golden Delicious have not been observed under all possible environmental conditions. The phenotype may vary somewhat with variations in environment such as temperature and light intensity without, however, any variance in genotype.

The following traits have been repeatedly observed and are determined to be the unique characteristics of 'Golden Delicious'. These characteristics in combination distinguish 'Golden Delicious' as a new and distinct *Salvia* cultivar:

1. Upright plant habit.
2. Freely branching habit.
3. Yellow green-colored foliage.
4. Numerous large red-colored flowers.

Plants of the new *Salvia* differ primarily from plants of the parent selection in leaf coloration as plants of the parent selection have green-colored leaves.

Plants of the new *Salvia* can be compared to plants of the *Salvia* cultivar Cambridge Blue, not patented. In side-by-side comparisons, plants of the new *Salvia* differed from plants of the cultivar Cambridge Blue in the following characteristics:

1. Plants of the new *Salvia* had yellow green-colored leaves whereas plants of the cultivar Cambridge Blue had green-colored leaves.
2. Plants of the new *Salvia* had red-colored flowers whereas plants of the cultivar Cambridge Blue had blue-colored flowers.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Salvia.*

The photograph at the bottom of the sheet comprises a side perspective view of a typical flowering plant of 'Golden Delicious' grown in a container.

The photograph at the top of the sheet comprises close-up views of typical flowers of 'Golden Delicious'.

DETAILED BOTANICAL DESCRIPTION

The aforementioned photographs and following observations and measurements describe plants grown in Bonsall, Calif., in a polyethylene-covered greenhouse during the winter with day temperatures ranging from 18° C. to 32° C. and night temperatures ranging from 13° C. to 21° C. Plants were grown in 15-cm containers and were about ten weeks old when the photographs and description were taken. Color references are made to The Royal Horticultural Society Colour Chart, 1995 Edition, except where general terms of ordinary dictionary significance are used.

Botanical classification: *Salvia elegans* cultivar Golden Delicious.

Parentage: Naturally-occurring whole plant mutation of an unnamed selection of *Salvia elegans,* not patented.

Propagation:

*Type.*—By cuttings.

*Time to initiate roots, summer.*—About 15 days.

*Time to initiate roots, winter.*—About 18 days.

*Time to produce a rooted young plant, summer.*—About 21 days.

*Time to produce a rooted young plant, winter.*—About 24 days.

*Root description.*—Fine, fibrous.

*Rooting habit.*—Freely branching; dense.

Plant description:

*Form.*—Perennial. Mostly upright plant habit to slightly outwardly spreading; narrow inverted triangle. Freely branching with about two primary stems each with about six to seven secondary lateral branches; moderately vigorous growth habit. Flowers arranged in verticillasters on spikes.

*Plant height.*—About 37 cm.

*Plant width.*—About 24 cm.

*Lateral branch description.*—Length: About 30 cm. Diameter: About 3 mm. Internode length: About 1.5 cm to 3.5 cm. Strength: Strong. Texture: Pubescent. Color, young: 145A. Color, woody: 200B.

*Foliage description.*—Arrangement: Opposite, simple. Length: About 4.7 cm. Width: About 2.3 cm. Shape: Elliptic to ovate. Apex: Acute. Base: Acute. Margin: Shallowly crenate. Texture, upper and lower surfaces: Pubescent; minute. Venation pattern: Pinnate; arcuate. Color: Developing and fully expanded foliage, upper surface: 144B; venation, 144B. Developing and fully expanded foliage, lower surface: 145A to more gray than 145A; venation, 145C. Petiole: Length: About 7 mm. Diameter: About 1 mm. Texture, upper and lower surfaces: Pubescent; minute. Color, upper and lower surfaces: 145B.

Flower description:

*Flower arrangement and shape.*—Single narrow tubular bilabiate flowers in verticillasters on spikes; flowers face mostly outwardly. Freely flowering habit, about 34 flowers per spike. Natural flowering season: Continuous from spring to late autumn in California.

*Flower longevity on the plant.*—Individual flowers last about five days on the plant. Flowers not persistent.

*Fragrance.*—None detected.

*Flower buds.*—Length: About 1.5 cm. Diameter: About 3 mm. Shape: Elongated oblong. Color: 46A.

*Inflorescence size.*—Length: About 14 cm to 21 cm. Diameter: About 3.5 cm.

*Flowers.*—Diameter: About 5 mm by 7 mm. Depth (height): About 3 cm.

*Petals.*—Arrangement: Narrowly tubular and bilabiate; petals fused at the base. Length, upper petal lobe: About 7 mm. Length, lower petal lobe: About 6 mm. Width, upper petal lobe: About 4 mm. Width, lower petal lobe: About 6 mm. Shape, lobes: Rounded. Apex: Rounded. Margin, upper and lower petals: Entire. Texture, outer surface: Pubescent. Texture, inner surface: Smooth. Color: When opening, outer surface: 46A. When opening, inner surface: 46D. Fully opened, outer surface: 53C. Fully opened, inner surface: 54C.

*Sepals.*—Arrangement: Five sepals fused at base. Length: About 4 mm. Width: About 2 mm. Shape: Elliptical. Apex: Acute. Margin: Entire. Texture, outer surface: Pubescent, minute. Texture, inner surface: Smooth, glabrous. Color, outer and inner surfaces: 145A.

*Peduncles.*—Strength: Strong. Length: About 5.5 cm. Diameter: About 2 mm. Aspect: Upright to about 45° from vertical. Texture: Pubescent, minute. Color: 145A.

*Pedicels.*—Strength: Moderately strong. Length: About 3 mm. Diameter: About 1 mm. Aspect: About 90° from the peduncle. Texture: Pubescent, minute. Color: 145A.

*Reproductive organs.*—Stamens: Quantity per flower: Two. Anther shape: Narrowly oblong. Anther size: About 2 mm by about 1 mm. Anther color: 46A. Pollen amount: Scarce. Pollen color: 12B. Pistils: Quantity per flower: One. Pistil length: About 3.2 cm. Stigma shape: Bi-parted. Stigma color: 46C. Style length: About 3 cm. Style color: 55D. Ovary color: 145C.

*Seed/fruit.*—Seed and fruit production has not been observed.

Disease/pest resistance: Plants of the new *Salvia* have not been noted to be resistant to pathogens and pests common to *Salvia*.

Temperature tolerance: Plants of the new *Salvia* have been observed to tolerate temperatures from about 0° C. to about 36° C.

It is claimed:

1. A new and distinct cultivar of *Salvia* plant named 'Golden Delicious', as illustrated and described.

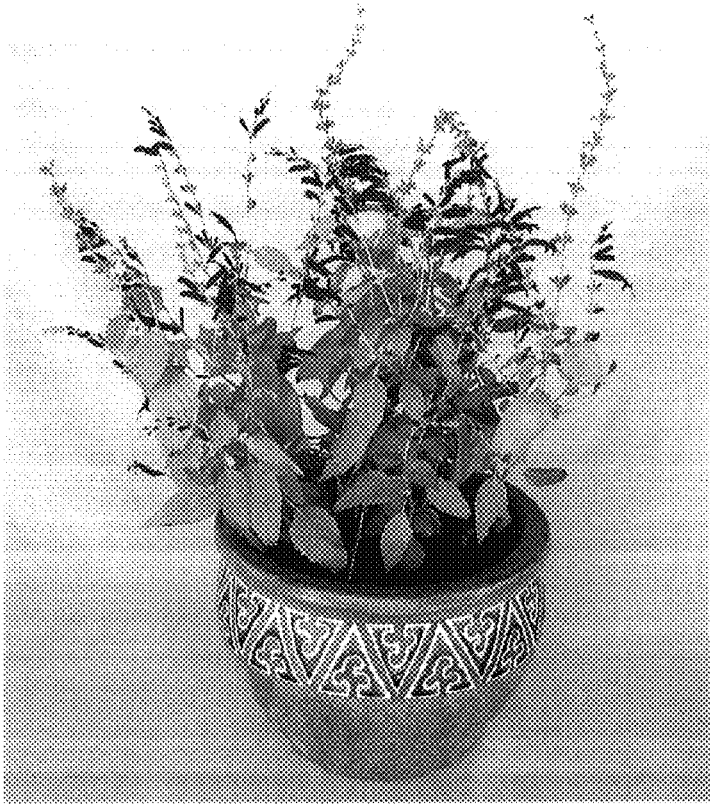
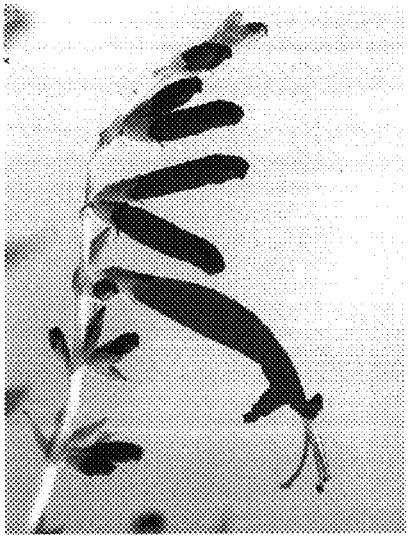

* * * * *